(12) United States Patent
Attia et al.

(10) Patent No.: US 8,491,657 B2
(45) Date of Patent: Jul. 23, 2013

(54) EXPANDING CAGE FOR VERTEBRAL SURGERY

(75) Inventors: David Attia, Montelimar (FR); Francisco Ros Guillen, Marignane (FR)

(73) Assignees: Gerald Schaumberg (FR), part interest; Francisco Ros Guillen (FR), part interest ( * ) Notice: Subject to any disclaimer, the term of this patent is extended or adjusted under 35 U.S.C. 154(b) by 742 days.

(21) Appl. No.: 12/593,575

(22) PCT Filed: Mar. 25, 2008

(86) PCT No.: PCT/FR2008/000395
§ 371 (c)(1),
(2), (4) Date: May 12, 2010

(87) PCT Pub. No.: WO2008/135669
PCT Pub. Date: Nov. 13, 2008

(65) Prior Publication Data
US 2010/0234956 A1 Sep. 16, 2010

(30) Foreign Application Priority Data
Mar. 28, 2007 (FR) .................................. 07 54090

(51) Int. Cl.
*A61F 2/44* (2006.01)
(52) U.S. Cl.
USPC ................................................ 623/17.16
(58) Field of Classification Search
USPC .......................................... 623/17.11–17.16
See application file for complete search history.

(56) References Cited

U.S. PATENT DOCUMENTS

| | | | | |
|---|---|---|---|---|
| 5,554,191 A * | 9/1996 | Lahille et al. | ............... | 623/17.11 |
| 5,653,763 A * | 8/1997 | Errico et al. | ............... | 623/17.11 |
| 6,102,950 A * | 8/2000 | Vaccaro | ..................... | 623/17.16 |
| 6,117,174 A * | 9/2000 | Nolan | ......................... | 623/17.11 |
| 6,685,742 B1 * | 2/2004 | Jackson | ..................... | 623/17.11 |
| 6,723,128 B2 * | 4/2004 | Uk | ............................ | 623/17.15 |
| 6,835,206 B2 * | 12/2004 | Jackson | ..................... | 623/17.11 |
| 7,220,280 B2 * | 5/2007 | Kast et al. | ................... | 623/17.11 |
| 7,431,735 B2 * | 10/2008 | Liu et al. | .................... | 623/17.11 |
| 7,655,043 B2 * | 2/2010 | Peterman et al. | ......... | 623/17.11 |
| 7,655,046 B2 * | 2/2010 | Dryer et al. | ................ | 623/17.15 |
| 8,221,501 B2 * | 7/2012 | Eisermann et al. | ........ | 623/17.11 |
| 2002/0040243 A1 | 4/2002 | Attali et al. | | |

(Continued)

FOREIGN PATENT DOCUMENTS

| | | |
|---|---|---|
| DE | 102005033608 A1 | 1/2007 |
| EP | 0 880 950 A1 | 12/1998 |
| EP | 1 415 622 A1 | 5/2004 |
| EP | 1 532 949 A1 | 5/2005 |
| WO | WO-98/10722 A1 | 3/1998 |

*Primary Examiner* — Mary Hoffman
(74) *Attorney, Agent, or Firm* — Blank Rome LLP (57) ABSTRACT

The disclosure relates to an expanding device intended to be implanted between the vertebral end-plates of two adjacent vertebrae, in particular for a stabilization operation for intervertebral fusion. The inventive device comprises: a cage forming a peripheral part that surrounds a central cavity, said peripheral part being formed by a leading edge and a thicker manipulation edge which are connected by two lateral edges provided with lateral housings; and a retractor received in the lateral housings, which can be moved between an insertion position, in which it is located close to the manipulation edge, and a locking position, in which it is located at the leading edge, increasing the height of same. The invention is characterized in that the retractor is provided with abutment means designed to maintain the retractor in the locking position and to oppose the release of the retractor from the cage.

12 Claims, 5 Drawing Sheets

U.S. PATENT DOCUMENTS

| | | |
|---|---|---|
| 2002/0116066 A1 | 8/2002 | Chauvin et al. |
| 2004/0127994 A1 * | 7/2004 | Kast et al. .................. 623/17.16 |
| 2006/0129244 A1 * | 6/2006 | Ensign ....................... 623/17.16 |
| 2006/0241774 A1 | 10/2006 | Attali et al. |

* cited by examiner

EXPANDING CAGE FOR VERTEBRAL SURGERY

CROSS-REFERENCE TO RELATED APPLICATIONS

This application is a National Phase Entry of International Application No. PCT/FR2008/000395, filed on Mar. 25, 2008, which claims priority to French Patent Application No. 0754090, filed on Mar. 28, 2007, both of which are incorporated herein by reference.

TECHNICAL FIELD OF THE INVENTION

The present invention relates to an implant used in vertebral surgery and more particularly for the treatment of cervical or lumbar intervertebral disc pathologies.

STATE OF THE ART

Such an implant is intended to be inserted between two cervical or lumbar vertebrae. It is aimed at restoring or maintaining the space corresponding to the treated vertebral disc and the anatomical situation of the latter so as to give the spine a natural curve and reopen the conjugation holes positioned on either side of the disc. Once the implant is positioned, a final fusion of both vertebrae is carried out by growing bones cells through the implant which is provided for this purpose with an internal cavity for receiving either natural or synthetic bone marrow, opened at each of the ends thereof to enable the contact of the graft with the respective vertebral bodies. The whole operation is known as a stabilisation operation for intervertebral fusion.

An implant for a stabilisation operation for an intervertebral fusion can be inserted by anterior route, i.e. it is introduced by the anterior part of the intervertebral space or by posterior route through the vertebral channel. The introduction by posterior route raises a certain number of problems, more particularly because nerves structures must be retracted. The introduction by anterior route is made complex by the fact that the intervertebral space is particularly narrow. The access can be facilitated using retracting surgical instruments, but the progression towards the posterior part of the space is difficult. The implant is generally positioned by impacts exerted on the ends thereof with a hammer. Then, it tends to sink into the posterior parts of the vertebral bodies without opening the conjugation holes and thus without enabling the decompression of the concerned nervous roots.

In addition, the existing implants tend to migrate and may in certain cases be expulsed because of the motions of the vertebrae. The implants known for an introduction by anterior route are generally of a quadrangular shape.

The application for patent WO98/10722 discloses an expanding implant including branches connected to one of the ends thereof through a base provided with an orifice which can be introduced by posterior route between the vertebral bodies of two consecutive vertebrae, so as to maintain them at a given distance and restore the stability of the spine. The branches and the base define a hollow cage which, in a rest position, has a cylindrical external profile and a conical internal profile. A wedge is adapted to be introduced into said cage, with the motion of said wedge inside said cage being adapted because of the conical internal profile of the latter to have said branches mutually retract.

The prior art also knows patent EP1415622 which discloses an expanding implant which can be introduced by posterior route between two bodies of two vertebrae and more particularly between two lumbar vertebrae. Between two successive vertebrae, two implants such as those described in patent EP1415622 are positioned side by side. The implants described in these two patents show a certain number of disadvantages. Generally speaking, they do not fill the vertebral space and provide a limited graft in surface. In addition, they are rather intended to be introduced by posterior route through the vertebral channel which implies a previous retraction of the nervous structures.

SUMMARY

One of the objects of the present invention is to provide an implant to be inserted by anterior route between the vertebral bodies of two adjacent vertebrae and be received in a stable way between these bodies while offering a large grafting surface. For this purpose, the invention relates to an expanding device intended to be implanted between the vertebral bodies of two adjacent vertebral, more particularly for an operation of stabilisation for an intervertebral fusion including:
  a cage composing a peripheral part enclosing a central cavity, the peripheral part being composed of a leading edge and a thicker handling edge connected by two side edges provided with side holes; and
  a retracting means received in the side holes, with the retracting means being movable between an insertion position, wherein it is close to the handling edge and a locking position, wherein it is at the level of the leading edge, the height of which it increases,
the retracting means being provided with stopping means selected for maintaining the retracting means in the locking position thereof and for opposing the expulsion of the retracting from the cage.

"Leading edge" means the edge which is intended to be inserted between the vertebral bodies whereas "handling edge" means the opposite edge on which the constraints (force or impact) intended to make the device sink between said vertebral bodies are generally exerted. The term "side edges" refers to the branches connecting the handling edge with the leading edge.

In the following, the term "longitudinal" refers to a direction which is parallel to the leading edge and the term "lateral" refers to a direction which is parallel to the side edges. Once implanted, the expanding device is positioned between two vertebral bodies, so that the plan formed by the side, the leading and the handling edges are parallel to the two vertebral bodies between which it is positioned. In addition, the term "height" indicates a dimension which is perpendicular to the plane formed by the side, leading and handling edges.

The implant according to the invention may thus have the shape of a generally quadrangular plane like in the prior art, but the section thereof has the general shape of a variable angular wedge that is a shape of a trapeze, the smaller base of which is of a variable size. In addition, the retracting means is provided with stopping means, making it possible to keep the retracting means in the locking position thereof, and more particularly to prevent the retracting means from leaving the cage at the end of the expansion. More particularly, the stopping means are opposed to the lateral expulsion of the retracting means. In addition, in a particular embodiment of the present invention, the stopping means are opposed to the expulsion of the retracting means through the leading edge. Advantageously, the leading edge includes a hole for receiving the retracting means so as to cause the height of the leading edge in its locking position to increase.

According to a preferred embodiment, the side holes are slots provided along the side edges and the retracting means is a rod, the ends of which are adapted to be inserted into the slots forming the side holes, with the dimensions of the ends of the rod being greater than the height of the slots so that the rod causes the increase, by a resilient deformation, of the height of the device at the level of the rod. In addition, the leading edge preferably includes a slot extending the slots forming the side holes, said slot being adapted for receiving the retracting means so as to cause the expansion of the leading edge. In addition, the hole of the leading edge is advantageously composed with a higher area of the slot of the leading edge. Advantageously, the slots forming the side holes have a decreasing height between the handling edge and the leading edge.

The slot of the leading edge connecting together the slots forming the side holes allows the progressive separation of the assembly formed by the side edges and the leading edge into two lugs, each of the lugs being parallel to the plan formed by the side edges, the leading edge and the handling edge and each of the lug protruding from a handling edge. During the progression of the retracting means from the insertion position to the locking position thereof, the height of the side holes progressively increases and the lugs are pushed away from each other. Advantageously, the stopping means are lateral ones and positioned at the ends of the rod engaged in the slots forming the side holes, with the edge of the rod being provided with side stops having a greater diameter and forming side locking means. This more particularly ensures that the rod remains parallel to the leading edge during its progression through the device.

In addition, the retracting means preferably includes two parts, with the part which is on the handling edge side being higher than the part which is on the leading edge side, so that the part which is on the handling edge side abuts against the leading edge, thus opposing the expulsion of the retracting means through the leading edge. Advantageously, the part of the retracting means which is on the handling edge side is comprised between the lateral edges. This part can further have a length which is substantially equal to that of the central cavity which enables it to provide a guiding function, thus making it possible for the retracting means to progress parallel to the leading edge when it passes from the insertion position to the locking position.

In addition, the retracting means includes a part comprised between the side edges and having a T-shaped section, with the foot of the T cooperating with the walls of the slot of the leading edge and the bar of the T abutting against the leading edge. Preferably, the part of the retracting which is on the leading edge side has a length which is equal to that of the leading edge, so that the part which is on the leading edge side supports the leading edge on the whole length thereof when the retracting means is in the locking position. Advantageously, the leading edge and the handling edge are longer than the side edges. Then, the implant has a shape close to that of the intervertebral disc which it is substituted for.

According to a preferred embodiment, said side edges are curved. More particularly, the side edges are formed so that the posterior lordosis of the device is substantially equal to 4° when the retracting means is in the locking position. Advantageously, the side edges substantially extend rectilinearly from the handling edge and then curve towards the leading edge.

According to one embodiment of the present invention, the leading edge and the side edges compose two upper and low U-shaped lugs connected to the handling edge and facing each other while defining the slots of the leading edge and the side holes between them. Advantageously, the upper lug includes a convex upper wall for the interface with the upper vertebral body, the lower lug including a concave lower wall for the interface with the lower vertebral body.

Advantageously, the cage is composed of one solid piece. Advantageously, the cage is made of polyetheretherketone (PEEK). In addition, the retracting means is preferably made of one solid piece.

The invention also relates to a surgical method for positioning, by the anterior route, an expanding device according to any one of the claims, to be substituted to a damaged vertebral disc between two cervical vertebrae including the following steps:
retraction of two cervical vertebrae,
removal of the damaged vertebral disc,
insertion of the expanding device through the leading edge thereof between two vertebrae, with the retracting means of the expanding device being in its insertion position, so that the expanding device occupies the whole surface initially occupied by the damaged intervertebral disc,
positioning of the retracting means in the locking position thereof.

BRIEF DESCRIPTION OF THE FIGURES

The present invention will be better understood upon reading the following description of a non limitative exemplary embodiment and referring to the appended drawings wherein.

DETAILED DESCRIPTION

Referring to FIGS. 1 to 6, an expanding device 1 is intended to be implanted between the vertebral bodies of two adjacent vertebrae, more particularly for the stabilisation for an intervertebral fusion. This device complies with one embodiment of the present invention, wherein the stopping means are lateral ones. As a whole, the device 1 is a cage shaped implant with an empty central space 16 defined by a peripheral frame including a handling edge 2, a leading edge 3 and two side edges 4, provided with side holes 5 adapted to receive retracting means 7 which can be moved from an insertion position shown in FIGS. 1, 3 and 5, wherein it is close to the handling edge, and a locking position shown in FIGS. 2, 4 and 6, wherein it is at the level of the leading edge the height of which is then increased so as to provide the locking implant between the bodies.

The implant 1 is made of a biocompatible elastic material adapted to expansion. Advantageously, this material has an elasticity module close to that of bones. Advantageously, this material is also radio-transparent. Advantageously, the implant is made of PEEK. Alternatively, it can also be made of metal such as titanium or of a resorbable material such as PLLA.

Figure 1:
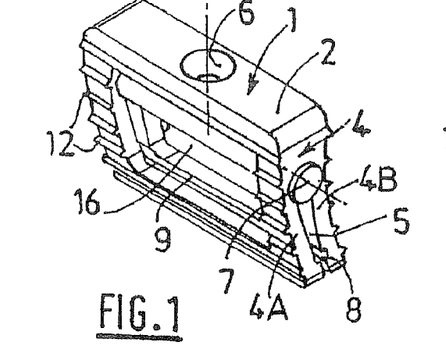
FIG. 1 is a schematic perspective view of an expanding device in the insertion position according to one embodiment of the present invention, wherein the rod stopping means are lateral ones.
Figure 2:
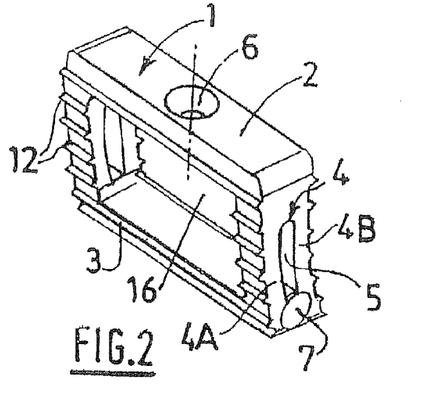
FIG. 2 is a view similar to that of FIG. 1 in the locking position.
Figure 3:
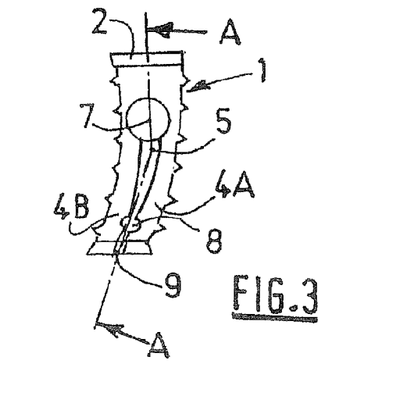
FIG. 3 is a plane side view of the device of FIG. 1.
Figure 5:
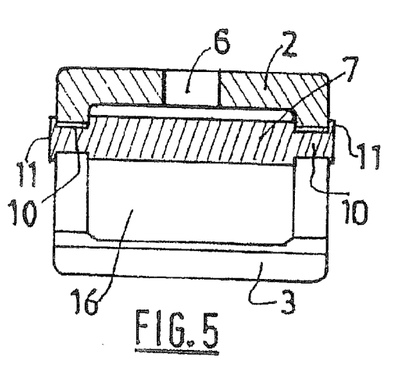
FIG. 5 is a sectional view along direction AA of the device of FIG. 3.
Figure 6:
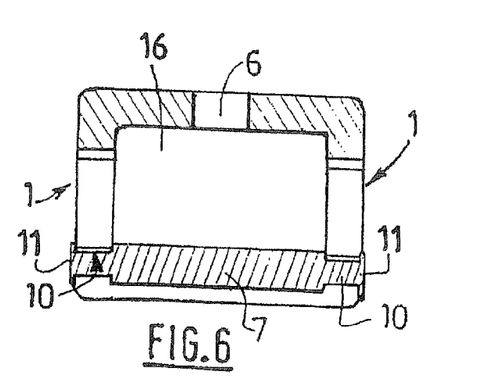
FIG. 6 is a sectional view along direction AA of the device of FIG. 4.
Figure 7:
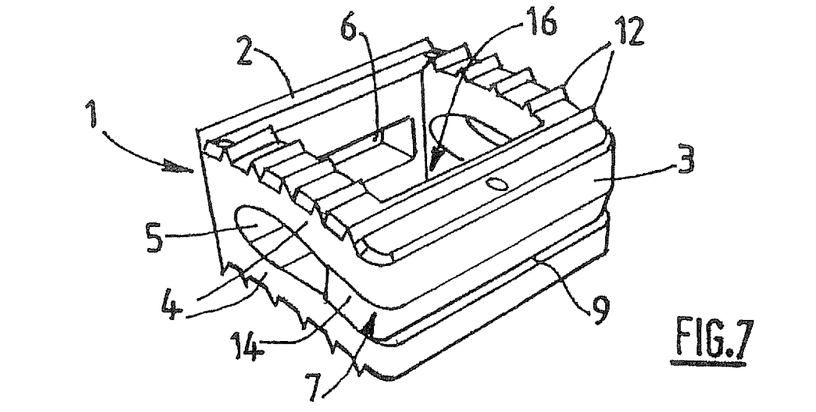
FIG. 7 is a perspective schematic view of an expanding device in the locking position according to another embodiment of the present invention, wherein the stopping means are positioned on the whole length of the rod.

FIGS. 1, 3 and 5 show the implant 1 in its insertion position. The implant 1 includes a leading edge 3 and a handling edge 2, the thickness of which is greater than that of the leading edge. The handling edge includes in its central part thereof a through hole 6 more particularly enabling to control the retracting means. The leading edge and the handling edge extend parallel and have the same length. However, the leading edge is slightly shifted upwards with respect to the handling edge, so that the side edges are curved, so as to reach the 4° lordosis upon completion of the expansion of the implant 1, so that the implant can follow the shape of the vertebral bodies, which enables the spine to restore its natural curvature. The curvature of the side edges is more precisely marked at the level of the leading edge. Generally speaking, the side edges extend substantially rectilinearly from the handling edge then curved towards said leading edge.

In addition, the leading edge and the handling edge are longer than the side edges, so as to better reproduce the shape of the vertebrae. The four edges thus form a rectangle which is longer than wide. Thus, the implant 1 has, in its insertion position, the general shape of a trapezoidal wedge, the end of which is slightly curved. This shape is selected to be adapted to the easiest possible insertion between the vertebral bodies.

The side holes are slots 5 provided on the side edges. These slots go through the side edges and have a decreasing height from top to bottom. They start at a higher position close to the leading edge 2, and they extend down to the bottom of the implant where they are extended at the level of the leading edge through a slot 9 which goes through the leading edge. Thus, the assembly composed of side edges and the leading edge is divided by various slots into two independent lugs 4A and 4B which can be retracted from each other. The wall of the lug 4A is convex, whereas the lower wall of the lug 4B is concave.

A hole 8 is provided for receiving the expansion device in locking position and is composed of a cylindrical area having a diameter which is greater than the thickness of the slot 9 provided at the level of a part of the latter being slightly above the median plane of the leading edge. The retracting means 7 is—as it can be better seen in FIG. 6—composed of a cylindrical rod, the edges of which 10 have a diameter which is smaller than that of the central part and is ended by stops, the diameter 11 of which is greater and forms side locking means.

As can be seen in the Figures, the central diameter of the rod 7 is greater than the height of the slot 9. The diameter of the ends 10 of such rod is greater than the height of the slot 5 at the level of the lower part of the implant and substantially equal to the height of these slots 5 at the level of the upper ends of these slots 5. When said rod is in the introduction position shown in FIGS. 1, 3 and 5, it has substantially no action on the side edges 4 and the implant substantially has the shape it would have without this rod. The progression of the rod will cause the progressive retraction of the lugs 4A and 4B, which means the increase in the height of the implant at the level of the area of the rod by a resilient deformation. This increase in height is maximum when the rod is in the locking position inside the hole 8. Optionally, the diameter of the ends 10 can be slightly greater than the height of the upper end of the slots 5, so as to slightly increase the height of the upper part of the side edges 4 in the implant insertion position. The selection of the material of the implant ensures that the deformation of the implant remains an elastic deformation whether that the amplitude of this deformation.

Figure 4:
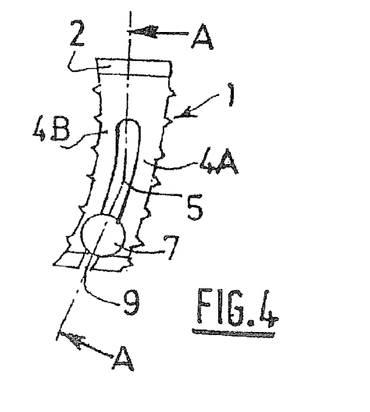
FIG. 4 is a plane side view of the device of FIG. 2.

In the locking position, as can be more particularly seen in FIG. 4, the height of the leading edge 3 is substantially equal to the height of the handling edge, which ensures an immobilisation of the implant between the two bodies. If so required, a rod diameter can be provided such that the fact of the leading edge remains slightly smaller than the height of the handling edge. Advantageously, the implant 1 includes teeth 12 intended to improve the fixing of the implant and the anchoring thereof on the faces thereof intended to contact the vertebral bodies.

The usual surgical technique imposes the utilisation of an intervertebral retracting means temporarily screwed on the vertebral bodies so as to detract the space and be able to remove the whole of the disc and insert the implant. The implant is inserted through the leading edge thereof with a force being exerted on the handling edge. Alternatively, the insertion can be obtained through impacts with a hammer applied on the handling edge. In the insertion position, the rod 7 abuts against the upper ends of the slots 5. The wedge shape of the implant then facilitates the insertion thereof.

When the implant is positioned, the rod 7 is moved and slides into the slots 5, then 9; until it reaches the hole 8. The handling of the rod can advantageously be obtained using a tool inserted through a hole 6. Advantageously, a guiding device (not shown) is provided in the implant position area. These can be cylindrical slides positioned on either side of the implant and cooperating with the spherical forms positioned on either side of the rods (instead of the stops 11). This can also be two parallel and integral rods introduced on either side of the hole 6.

The progression of the rod will retract the two lugs 4A and 4B from each other, so that the profile of the implant will progressively evolve from the shape represented in FIG. 3 to the shape represented in FIG. 4, wherein the height of the implant is substantially the same on the whole length thereof. At the end of the travel, the rod is anchored inside the leading edge 3 and thus becomes a rigid structure thereof making said edge compression-resistant. This expansion of the implant makes it possible to anchor it in the vertebral bodies, to retract the posterior part of the intervertebral space and thus to widen in height the conjugation channels and give space to the corresponding compressed nerves. It releases an internal space capable of receiving an autologous or artificial bone graft.

Figure 8:
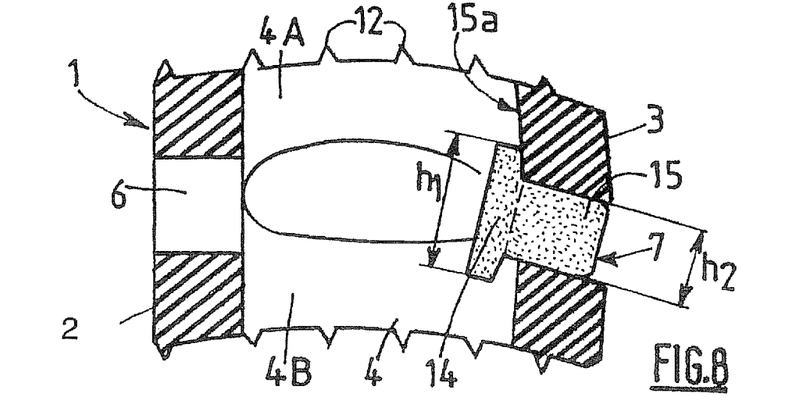
FIG. 8 is a cross-sectional view of the device of FIG. 7.
Figure 9:
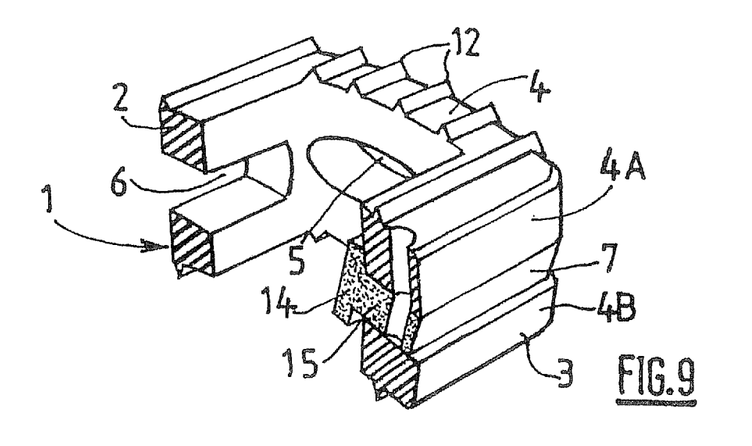
FIG. 9 is a perspective view of a section of the device of FIG. 7.
Figure 10:
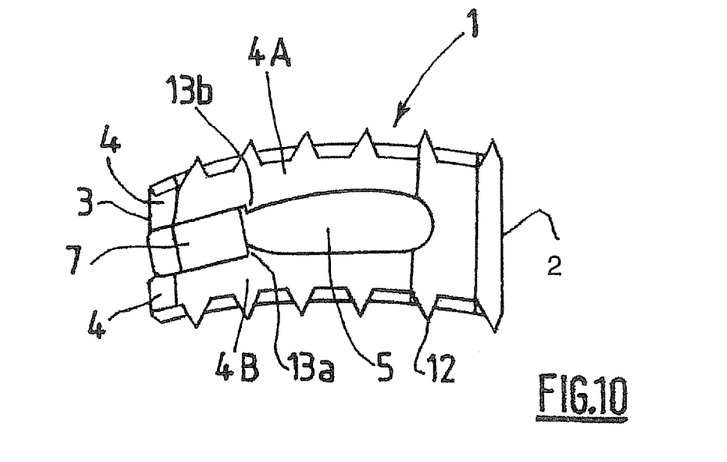
FIG. 10 is a side view of the device of FIG. 7 in the locking position.

FIGS. 7 to 17 show an implant according to another embodiment of the present invention, wherein the retracting means shows a stopping means having the shape of a T in FIG. 8, with said stopping means opposing the expulsion of the retracting means through the leading edge. The same numbers are used for the common elements with the previous embodiment and references will be easily made to the description of the first embodiment for some details. More particularly, the side, leading and handling edges are the same as in the preceding embodiments. In this embodiment, only the retracting means which is different from that of the previous embodiment will be disclosed in greater details.

Thus, the retracting means 7 in FIGS. 7 to 17 includes a part which is comprised between the side edges 4 and has a T-shaped section. The retracting means is a rod including two globally parallelepiped parts 14 and 15, so that the height of the part 14 is greater than the height of the part 15. As a matter of fact, the part 14 has a height h1 and the part 15 has a height h2, so that h1 is greater than h2. In addition, the part 15 of the retracting means 7 has a length L1 equal to the length L3 of the leading edge 3. The part 14 of the retracting means 7 has a length L2 which is slightly smaller than the length L4 of the central cavity of the implant 1.

Figure 11:
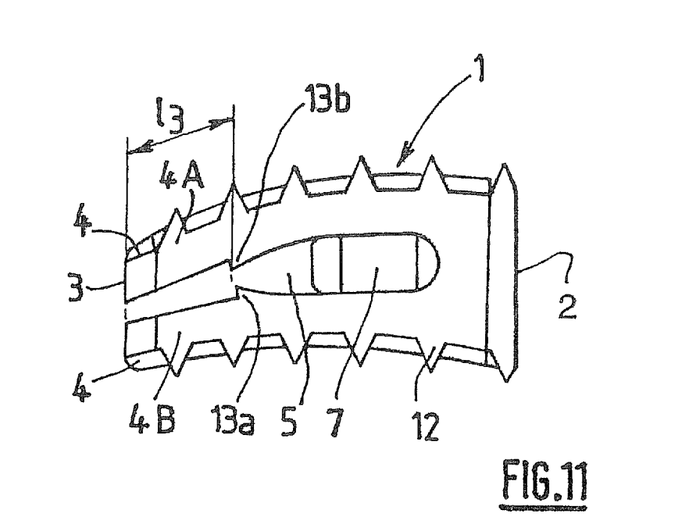
FIG. 11 is a side view of the device of FIG. 7 in insertion position.
Figure 12:
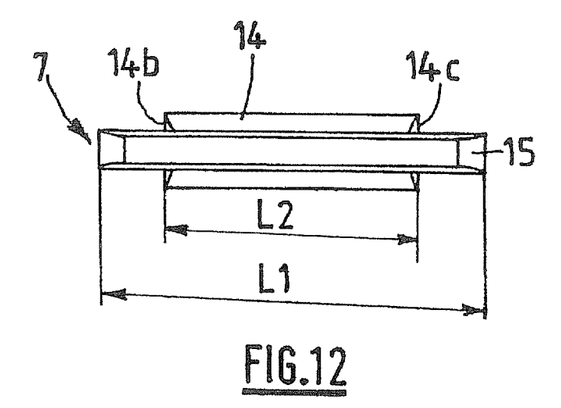
FIG. 12 is a face view of the retracting means according to the embodiment of FIG. 7.
Figure 13:
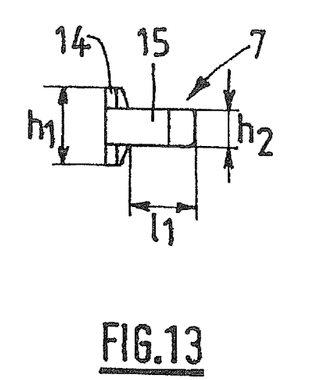
FIG. 13 is a side view of the retracting means according to the embodiment of FIG. 7.
Figure 14:
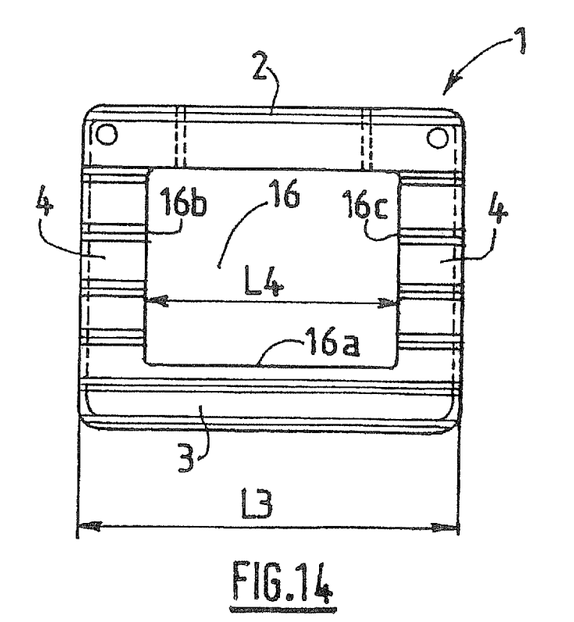
FIG. 14 is a top view of the device of FIG. 7.
Figure 15:
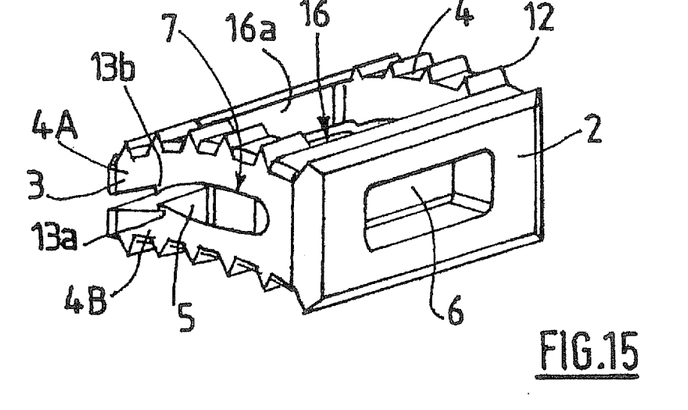
FIG. 15 is a perspective view of the device of FIG. 7 in the locking position.
Figure 16:
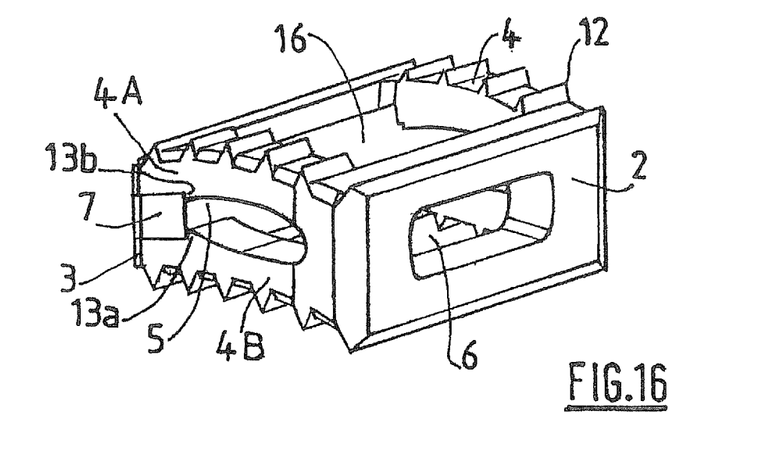
FIG. 16 is a perspective of the device of FIG. 7 in the insertion position.

Initially, the retracting means 7 is in an insertion position which is visible in FIGS. 11 and 16, wherein it is close to the handling edge 2. The part 14 is in the central cavity 16, so that it has no action on the side edges, whatever the position of the retracting means 7. In addition, the height h2 is so that in this insertion position, the retracting 7 has no action on the side edges 4 and the implant 1 has the shape it would have without this retracting means 7.

When the retracting means 7 is pushed to be closer to the leading edge 3, the part 14 of the retracting means 7 moves in the central cavity 16 of the implant 1, so that the retracting means 7 has no action on the side edges 4. On the contrary, the part 15 of the retracting means 7 progressively retracts the lugs 4A and 4B by a resilient deformation and thus increases the height of the side holes 5. This increase in height goes on until the part 15 of the retracting means 7 reaches the leading edge 3, at the level of which the retracting means 7 is stopped by the part 14. As a matter of fact, the part 15 has a width 11 which is substantially equal to the width 12 of the leading edge and the internal part 16a of the central cavity 16, so that, when the part 15 of the retracting means 7 reaches the leading edge 3, the part 14 of the retracting means 7 reaches the internal wall 16a. The part 14 thus abuts against the wall 16a of the central cavity 16, which locks the progression of the retracting means 7. The part 14 of the retracting means 7 thus opposes the expulsion of the retracting means 7 through the leading edge.

In addition, each of the internal walls of the side edges is provided with a step forming a stop 13a or 13b, located at a distance 13 from the outside of the upper leading edge or equal to the width 11 of the part 15 of the retracting means 7. Such stops oppose a return of the retracting means 7 to its insertion position.

In addition, the side walls 14b and 14c of the part 14 of the retracting means 7 are parallel to each other and parallel to the side walls 16b and 16c of the central cavity. These walls form stops opposing the side expulsion of the retracting means 7. The side walls 14b and 14c are, in addition, separated by a distance which is slightly smaller than the distance separating the walls 16b and 16c of the central cavity, so that the walls 14b and 14c of the part 14 guide the retracting means 7 upon the passage thereof from its insertion position to its locking position.

In addition, the part 15 has a length L1 equal to the length L3 of the leading edge, which makes it possible to reinforce the mechanical resistance of the implant 1, since the part 15 of the retracting means 7 thus supports the leading edge on the whole length thereof.

Many alternative solutions are possible, of course. Thus, the retracting means 7 can have various forms, and it can for example combine side and longitudinal stopping means. In addition, the implant can be made of any elastic biocompatible material, made of one or several pieces. In addition, the implant can be made in a plastically deformable material, when the risk of its being removed is small.

The invention claimed is:

1. An expanding device (1) to be implanted between vertebral bodies of two adjacent vertebrae, the expanding device including:
    a cage surrounding a central cavity and defining a peripheral part therearound the cage having:
        a leading edge (3),
        a handling edge (2) thicker than the leading edge, and,
        two elongated side edges (4), each provided with a respective side holes (5) and extending laterally between said handling edge and leading edge ; and
    a retracting means (7) received in the side holes (5), said retracting means (7) being movable between an insertion position, wherein the retracting means is close to the handling edge and a locking position wherein the retracting means engages the leading edge, causing an expansion of said leading edge, wherein:
    the retracting means (7) is provided with stopping means adapted for maintaining the retracting means (7) in the locking position and for preventing the retracting means from being expulsed from the cage,
    the leading edge includes two lateral slots (9) receiving the retracting means (7) in the locking position, so as to cause said expansion of the leading edge (3); and
    the retracting means includes two parts each having a T-shaped section, each T-shaped section having a central foot and a bar, the central foots engaging walls of the respective lateral slots (9) and the T bars abutting against the leading edge (3).

2. An expanding device according to claim 1, characterised in that the stopping means oppose the side expulsion of the retracting means.

3. An expanding device according to claim 1, characterised in that the stopping means oppose the expulsion of the retracting means (7) through the leading edge (3).

4. An expanding device according to claim 1, characterised in that the leading edge (3) includes a hole (8) for receiving the retracting means (7), so as to cause the leading edge in the locking position to expand.

5. A device according to claim 1, characterised in that the handling edge and the leading edge are both longer than the side edges.

6. A device according to claim 1, characterised in that the side edges (4) are curved.

7. A device according to claim 1, having a posterior lordosis substantially equal to 4°, when the retracting means is in the locking position.

8. A device according to claim 6, characterised in that the side edges (4) substantially extend rectilinearly from the handling edge (2) and then are curved towards the leading edge (3).

9. A device according to claim 1, characterised in that the cage is made in one solid piece.

10. A device according to claim 1, characterised in that the retracting means (7) is made in one solid piece.

11. A surgical method for positioning, by anterior route, an expanding device for the substitution of an intervertebral disc between two adjacent cervical vertebrae respectively having an upper vertebral body and a lower vertebral body, the expanding device comprising:
    a cage surrounding a central cavity, said cage having a leading edge (3), a handling edge (2) and two side edges (4) along each of which extend upper and lower lugs separated by a slot (9) which also extends in the leading edge, said upper lug (4A) including an upper convex wall and said lower lug (4B) including a concave lower wall, and, a retracting means (7) movable between an insertion position, wherein the retracting means is close to the handling edge and a locking position wherein the retracting means engages the leading edge, the method including the following steps:

retracting said two adjacent cervical vertebrae, removing the intervertebral disc, inserting the expanding device through the leading edge between the two adjacent cervical vertebrae, with the retracting means (7) of the expanding device being in the insertion position, and the upper convex wall engaging the upper vertebral body, and the concave lower wall engaging the lower vertebral body, and, positioning of the retracting means (7) in the locking position.

12. An expanding device to be implanted between upper and lower vertebral bodies of two adjacent vertebrae, the expanding device including:

a cage surrounding a central cavity and defining a peripheral part therearound, the cage having:

a leading edge (3), a handling edge (2) thicker than the leading edge, and, two elongated side edges (4), each provided with a respective side hole (5) and extending laterally between said handling edge and leading edge ; and a retracting means (7) received in the side holes (5), said retracting means (7) being movable between an insertion position, wherein the retracting means is close to the handling edge and a locking position wherein the retracting means engages the leading edge, causing an expansion of said leading edge, wherein:

along each side edge extend upper and lower lugs separated by a slot (9) which also extends in the leading edge, said upper lug (4A) including an upper convex wall for engaging the upper vertebral body, and said lower lug (4B) including a concave lower wall for engaging the lower vertebral body.

\* \* \* \* \*

UNITED STATES PATENT AND TRADEMARK OFFICE
CERTIFICATE OF CORRECTION

| | | |
|---|---|---|
| PATENT NO. | : 8,491,657 B2 | Page 1 of 1 |
| APPLICATION NO. | : 12/593575 | |
| DATED | : July 23, 2013 | |
| INVENTOR(S) | : David Attia et al. | |

It is certified that error appears in the above-identified patent and that said Letters Patent is hereby corrected as shown below:

On the title page, Item (73) Assignee should read

-- David Attia (FR) part interest;
Gerald Schaumberg (FR) part interest;
Francisco Ros Guillen (FR) part interest --

Signed and Sealed this
Twenty-eighth Day of January, 2014

Michelle K. Lee
*Deputy Director of the United States Patent and Trademark Office*